(12) United States Patent
Leonard et al.

(10) Patent No.: US 8,889,579 B2
(45) Date of Patent: Nov. 18, 2014

(54) PROCESS FOR MANAGING SULFUR ON CATALYST IN A LIGHT PARAFFIN DEHYDROGENATION PROCESS

(75) Inventors: Laura E. Leonard, Western Springs, IL (US); Gregory J. Gajda, Mount Prospect, IL (US); Steven C. Kozup, Chicago, IL (US)

(73) Assignee: UOP LLC, Des Plaines, IL (US)

( * ) Notice: Subject to any disclaimer, the term of this patent is extended or adjusted under 35 U.S.C. 154(b) by 228 days.

(21) Appl. No.: 13/424,874

(22) Filed: Mar. 20, 2012

(65) Prior Publication Data

US 2013/0252801 A1   Sep. 26, 2013

(51) Int. Cl.
| | |
|---|---|
| *B01J 38/04* | (2006.01) |
| *B01J 38/12* | (2006.01) |
| *B01J 38/18* | (2006.01) |
| *B01J 38/10* | (2006.01) |
| *C10G 35/09* | (2006.01) |
| *B01J 27/32* | (2006.01) |
| *B01J 23/96* | (2006.01) |

(52) U.S. Cl.
CPC ............... *C10G 35/09* (2013.01); *B01J 27/32* (2013.01); *B01J 38/10* (2013.01); *B01J 23/96* (2013.01)
USPC ............. 502/53; 502/34; 502/38; 502/50

(58) Field of Classification Search
CPC .......... B01J 38/10; B01J 23/96; B01J 27/32; C10G 35/09; Y10S 502/517
USPC ......................................... 502/20–56
See application file for complete search history.

(56) References Cited

U.S. PATENT DOCUMENTS

| | | | | |
|---|---|---|---|---|
| 3,935,244 | A | * | 1/1976 | Hayes ............................ 502/37 |
| 4,033,898 | A | | 7/1977 | Jacobson |
| 5,000,841 | A | * | 3/1991 | Owen ........................... 208/113 |
| 5,270,272 | A | | 12/1993 | Galperin |
| 5,880,050 | A | | 3/1999 | Boitiaux |
| 2004/0043890 | A1 | | 3/2004 | Robinson |
| 2013/0252801 | A1 | * | 9/2013 | Leonard et al. ................. 502/53 |

FOREIGN PATENT DOCUMENTS

| | | |
|---|---|---|
| RU | 2096085 C1 | 11/1997 |
| RU | 2157728 C1 | 10/2000 |
| SU | 910184 A1 | 3/1982 |
| SU | 1720708 A1 | 3/1992 |

OTHER PUBLICATIONS

PCT International Search Report for PCT/US/2013/029235, mailing date Aug. 29, 2013.

* cited by examiner

*Primary Examiner* — Jennifer A Smith
(74) *Attorney, Agent, or Firm* — Arthur E Gooding

(57) ABSTRACT

A process is presented for the management of sulfur on a catalyst. The catalyst is a dehydrogenation catalyst, and sulfur accumulates during the dehydrogenation process. Sulfur compounds are stripped from the spent catalyst and the catalyst is cooled before the regeneration process. The process includes controlling the amount of sulfur that needs to be removed from the catalyst before regeneration.

16 Claims, 1 Drawing Sheet

PROCESS FOR MANAGING SULFUR ON CATALYST IN A LIGHT PARAFFIN DEHYDROGENATION PROCESS

FIELD OF THE INVENTION

The present invention relates to dehydrogenation processes, and in particular to the regeneration of catalysts used in dehydrogenation processes.

BACKGROUND OF THE INVENTION

Light olefins can be produced through the dehydrogenation of light paraffins. The dehydrogenation of paraffins is performed in a catalytic process where a hydrocarbon stream comprising paraffins is contacted with a dehydrogenation catalyst in a reactor under dehydrogenation conditions to generate a light olefin product stream. The catalyst used in this process includes a catalytic metal on a support. The catalytic metal generally comprises a noble metal, such as platinum or palladium. The dehydrogenation process involves many reactions and during the dehydrogenation process, the catalyst is slowly deactivated through the reaction process. One of the contributors to the deactivation is the generation of coke on the catalyst. The catalyst therefore, needs to be periodically regenerated to remain useful in the dehydrogenation process. Due to the high temperatures required for the production of light olefins in the dehydrogenation reactors, a low level of $H_2S$ must be maintained in the reactor section to prevent the formation of metal catalyst coke. In the case of light paraffin dehydrogenation the sulfur level is controlled by directly injecting a sulfur containing compound such as dimethyl disulfide into the reactor section with the hydrocarbon feed. Sulfur is known to passivate metal surfaces thus preventing metal catalyzed coke formation. The sulfur can be carried into the regenerator by catalyst and over time impact the catalyst performance. This control and regeneration of a catalyst is important for the lifespan of the catalyst and its usefulness in a catalytic process.

SUMMARY OF THE INVENTION

The present invention provides for improved sulfur management in a dehydrogenation reactor system. Sulfur is used for passivation of the metal surfaces to limit metal catalyzed coking. However, sulfur accumulates on the catalyst from sulfur in the feed to the reactors. The process includes managing the sulfur by removal of the sulfur from spent catalyst by passing the spent catalyst to a sulfur stripping vessel. The sulfur stripping vessel has hot hydrogen gas passed to remove sulfur compounds from the spent catalyst to generate a stripped catalyst stream. The stripped catalyst stream is passed to a cooling section wherein a cooling gas is passed over the catalyst. The catalyst is cooled before sending the stripped catalyst to a regeneration unit. The stripped catalyst is passed to the regeneration unit, and the catalyst is regenerated. The regenerated catalyst is returned to the dehydrogenation reactor system via the reduction zone. In the reduction zone, the regenerated catalyst is contacted with hydrogen to reduce the catalytic metals which are oxidized in the regenerator.

Other objects, advantages and applications of the present invention will become apparent to those skilled in the art from the following detailed description and drawings.

DETAILED DESCRIPTION OF THE INVENTION

Figure 3:
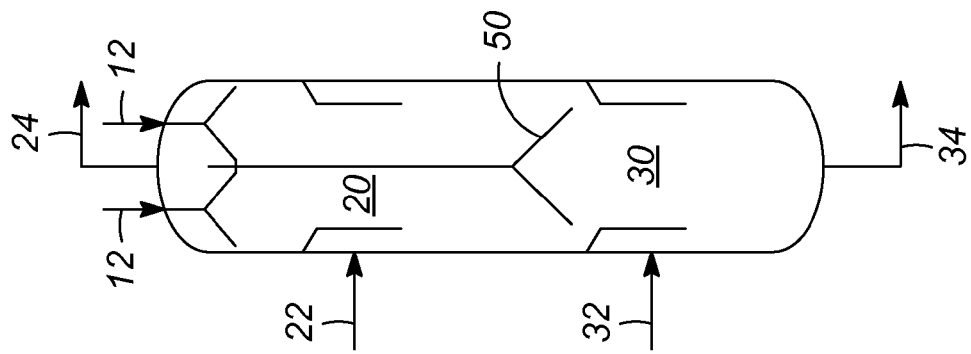
FIG. 3 is a third design for the catalyst stripping and cooling unit.

Catalysts are very sensitive to poisons. Catalysts are very expensive, and among the most expensive items in a petrochemical plant. Poisons can accelerate the deactivation of the catalyst, and in some instances the deactivation is sufficient to require catalyst replacement. The controlling of the levels of catalyst poisons in a process can lead to increased catalyst life and improved productivity while generating catalyst savings. In particular, dehydrogenation catalysts that incorporate platinum (Pt) for the active metal component are sensitive to sulfur. While platinum is referred to in the description, it is intended that any platinum group metal can be included in this description. Sulfur is a cause for the accelerated deactivation of dehydrogenation catalysts used in paraffin dehydrogenation, and in particular for platinum based catalysts. However, sulfur is also used to passivate the metal surfaces to limit the metal catalyzed coking. The balance of passivation versus deactivation is important to maintain the useful catalyst life. During the dehydrogenation process, a small amount of sulfur is injected for passivation purposes. The sulfur will build up over time, and will have a significant sulfur concentration on the catalyst which can be as high as 0.1 to 1 wt % on the spent catalyst, or more commonly in the range of 0.1 to 0.5 wt %. Consequently sulfur also needs to be removed to limit the amount of sulfur in the regenerator, reduction zone, and entering the reaction zone.

In a normal process, the catalyst is continuously circulated between the dehydrogenation reactor and the regenerator. The catalyst accumulates coke during the dehydrogenation process and the regenerator burns off the coke and the platinum is re-dispersed over the catalyst surface. Platinum re-dispersion is commonly carried out using a process referred to as oxy-chlorination, wherein the catalyst is contacted with a halogen containing gas at elevated temperatures. The halogen is usually chlorine. The sulfur that is present on the catalyst entering the regenerator is converted from sulfides to sulfates in the burn zone of the regenerator. It has been found that more severe conditions, i.e. higher temperatures and longer residence times, are required to strip sulfate from the catalyst as compared to sulfide using the same hydrogen rich stripping gas. It is therefore desirable to strip sulfur from the catalyst prior to oxygen exposure in the regenerator section where it is converted from sulfide to sulfate. The catalyst exiting the burn zone, and the platinum re-dispersion zone, have been observed to have sulfates present on the catalyst, and to have a surface enrichment of sulfur. This sulfur has also been observed to displace chlorides leading to skewed sulfur profiles and correlating to skewed chloride profiles. There is further evidence that the sulfur contributes to the migration of platinum on the catalyst surface by creating an energy gradient during platinum re-dispersion. This bulk migration leads to platinum migration and accelerated deactivation of the catalyst.

The process often includes contacting the spent catalyst, prior to passing the catalyst to the regenerator, with a reduction zone effluent gas to adsorb chloride stripped from the catalyst in the reduction zone. This reduces the chloride load on the downstream chloride treater and increases the chloride treater adsorbent bed life.

The sulfur that remains on the regenerated catalyst as the catalyst is lifted to the reduction zone is in the form of a sulfate and can be present in a relatively high concentration, ranging from 0.05 wt % to 1 wt % of the catalyst, or more commonly in the range from 0.05 to 0.5 wt %. The sulfate can be reduced to a sulfide and then stripped off the catalyst with hydrogen if the catalyst is heated to an elevated temperature for a sufficient time. One problem with this process is that in the reduction zone, a substantial amount of water and hydrogen sulfide ($H_2S$) is generated. The water, when present in relatively high concentrations, contributes to platinum agglomeration, and the agglomeration reduces the activity of the catalyst. The water, when present in relatively high concentrations, may also impact the interaction of Pt with other catalytic components of the catalyst, adversely impacting the catalyst performance by decreasing activity or increasing side reactions such as coking.

The elevated $H_2S$ concentration in the reduction zone effluent may further degrade the catalyst if it is contacted with the spent catalyst to adsorb HCl that is liberated in the chlorination zone by further increasing the sulfur passed to the regenerator with the catalyst. The problems associated with stripping the sulfate from the catalyst in the reactor section are equally undesirable. One consequence is the potential for a local increase in $H_2S$ and water concentrations which can accelerate corrosion of process equipment and the accumulation of tramp, or undesirable stray, metals on the catalyst. In addition, the water generated by the reduction of sulfate can increase the chloride loss, and therefore increase the chloride concentration in the reactor effluent. This shortens the chloride treater life.

Sulfur is a necessary component of the feedstock, and the sulfur on the catalyst cannot be removed or reduced through simply eliminating the sulfur injection. Sulfur management is important for a long catalyst life. The present invention seeks to improve the sulfur management and avoids the problems associated with high sulfur concentrations in the regenerator and the reduction zone by stripping the sulfur from the spent catalyst before passing the spent catalyst to the regenerator. The process comprises passing the spent catalyst to a sulfur stripping vessel. A hydrogen rich gas stream is passed to the stripping vessel at an elevated temperature to contact the catalyst and strip sulfur and sulfur compounds from the catalyst, to generate a stripped spent catalyst stream. The stripped spent catalyst stream is passed to a catalyst cooler to cool the catalyst. The catalyst cooler has a cooled gas passed over the catalyst to reduce the temperature of the catalyst before passing the spent catalyst to the regenerator. The stripped spent catalyst stream is passed to the regenerator and a regenerated catalyst stream is generated. The regenerated catalyst is returned to the dehydrogenation reactor via the reduction zone. The reduction zone returns any metal on the catalyst to its metallic state.

The spent catalyst is stripped with a heated hydrogen rich gas stream, where the temperature is at least 150° C., with a preferred temperature greater than 250° C., and a more preferred temperature greater than 300° C. The hydrogen rich stripping gas will contain greater than 50 mol % hydrogen, preferably greater than 80 mol % hydrogen, and more preferably greater than 90 mol % hydrogen. In general, it has been found that for 30 minutes residence time in the sulfur stripping zone, approx. 30% of the sulfide is removed at 150° C., and approx. 85% of the sulfide is removed at 250° C. Increasing the temperature of the gas or the residence time further increases the extent of sulfur removal. The preferred conditions are to have the catalyst reside in the sulfur stripping vessel as a sufficiently high temperature to reduce and remove at least 90% of the sulfur from the catalyst. The residence time in the stripping vessel is related to the temperature for stripping, where as the stripping temperature is increased, the residence time can be reduced. After stripping the catalyst for a sufficient time in the sulfur stripping vessel, the catalyst is passed to a catalyst cooling unit. The catalyst is typically cooled to a temperature less than 200° C. to protect downstream catalyst handling equipment. Preferably, the catalyst is cooled to a temperature between 100° C. and 150° C.

While the stripping and cooling can be performed with different vessels, combining the sections into a single vessel allows for better material handling and reduces the number of process vessels that must be purchased and maintained. When retrofitting of existing dehydrogenation processes separate vessels can be used, where an additional vessel or two can be added at the catalyst outlet of the last reactor in the dehydrogenation reactor system.

In one embodiment, the process includes passing the stripped spent catalyst to a vessel containing a cooling zone, where the catalyst is contacted with the reduction zone effluent. The stripped spent catalyst adsorbs chloride that had been liberated in the reduction zone. While chloride ions are the main halogen ions liberated in this zone, other halogen ions that might be present can also be adsorbed and removed from the catalyst. The stripped and cooled spent catalyst is then passed to the regenerator along with the adsorbed chloride or alternative halogen.

Figure 2:
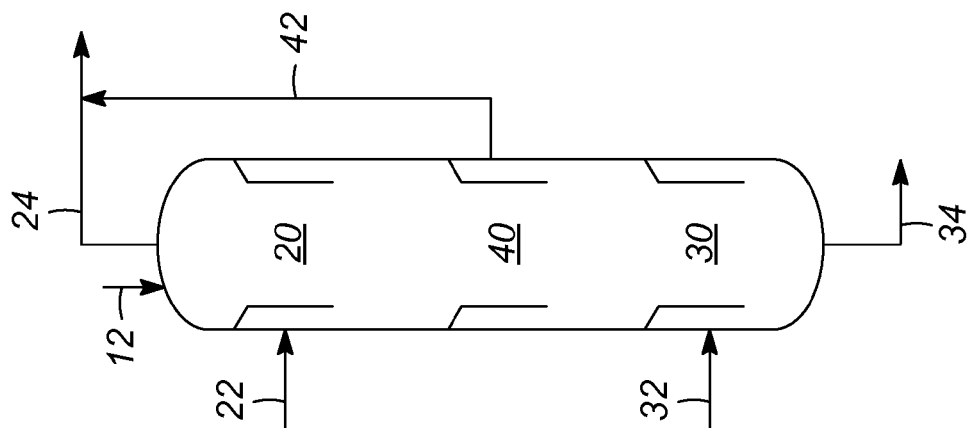
FIG. 2 is an alternate embodiment for the catalyst stripping and cooling unit.
Figure 1:
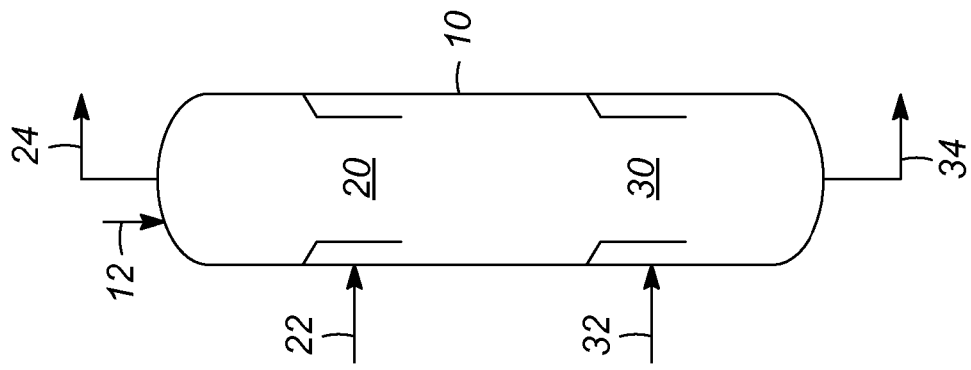
FIG. 1 is a diagram of an elongated catalyst collector.

The process can be seen in the FIG. 1. A dehydrogenation process can comprise a plurality of dehydrogenation reactors, or a single dehydrogenation reactor. The system, and process, utilizes a moving bed reactor system, where catalyst flows through the reactors. The catalyst upon leaving a reactor is collected and passed to a subsequent reactor in a reactor system. The catalyst leaving the last reactor is collected and passed to a regeneration system. Before passing the catalyst to the regeneration system, the catalyst leaving the last reactor is passed to a catalyst collector 10, which has been modified for pretreatment of the catalyst before passing the catalyst to the regenerator. The catalyst collector 10 is a combination stripping and cooling vessel. The catalyst collector 10 is positioned in fluid communication with the catalyst outlet from the last reactor, and catalyst flows downward through a first stripping section 20, then to a cooling section 30. Spent catalyst is passed to the vessel through one or more catalyst entry ports 12, and flows to the stripping section 20. A substantially sulfur free hydrogen rich gas is passed through the stripping gas port 22 to the stripping section 20, removing a portion of the sulfur compounds on the spent catalyst. Preferably, the substantially sulfur free hydrogen rich gas has less than 100 ppm by vol. $H_2S$. The stripped catalyst flows to the cooling section 30. A cooling gas is passed to the cooling section 30 through a cooling gas port 32, and flows over the catalyst to cool the catalyst. The cooled catalyst is passed out the cooled catalyst port 34 to a catalyst regenerator. The combined stripping gas and cooling zone effluent is passed out of the vessel through a gas exit port 24. The catalyst is regenerated in the regenerator and passed back to the first reactor in the dehydrogenation reactor system via the reduction zone. The stripping gas and cooling gas effluents may be combined within the catalyst collector 10 or external to the catalyst collector 10, wherein the vessel includes one or more gas outlets. An alternate design is shown in FIG. 2, where the vessel includes a separation zone 40. The separation zone 40 is between the stripping zone 20 and the cooling zone 30, and is a region where the cooling gas substantially separates from the catalyst and flows out a cooling effluent port 42. As an option, the cooling effluent and the stripping gas 24 can be combined outside the vessel. The separation zone 40 provides for removal of the cooling gas, and in turn reduces the stripping gas load in the stripping section 20. The load is reduced by limiting the cooling gases flowing into the stripping zone 20 and reducing temperatures during the stripping process. Another alternate design is shown in FIG. 3, where the stripping gas 22 enters and mixes with the catalyst entering from above in 12. The catalyst and stripping gas disengage at a position below the stripping section 20, and the stripped gas and cooling gas are collected at a separate collection device 50, and passed through one or more gas exit ports 24. Stripping gas also flows upward through the stripping section 20, and is collected above the stripping section 20. The stripping gas is then passed out through the gas exit ports 24 with the cooling gas. In both these alternatives, the stripped catalyst is passed to a cooling zone 30 and contacted with a cooling gas. The optional designs may include internals to reduce, or minimize, the amount of cooling gas entering the stripping zone 20, and to limit or minimize the amount of stripping gas from entering the cooling zone. The internals may include one or more vapor collection zones having vapor tunnels, baffles, or combinations thereof.

The hot stripping gas can be hydrogen generated by the dehydrogenation process and can be heated to a preferred temperature prior to passing the hot gas to the stripping section 20. In an alternative embodiment, the hot stripping gas can be an effluent gas from the reduction zone if the spent catalyst has been sulfur stripped. The cooling gas may be hydrogen generated by the dehydrogenation process and can be cooled to a preferred temperature prior to passing the cooling gas to the cooling zone 30. In an alternative embodiment, the cooling gas can be an effluent gas from the reduction zone. The regenerated catalyst is passed to the reduction zone prior to being passed to the dehydrogenation reactors. The purpose of the reduction zone is to reduce the catalytic metal on the catalyst prior to passing the catalyst to the dehydrogenation reactors. Excess halogens may be stripped from the catalyst in the reduction zone. Typically, excess chloride is stripped in the form of HCl. By directing the reduction zone effluent gas to the cooling zone, the chloride may be adsorbed on the stripped spent catalyst.

Optional embodiments include directing the reduction zone effluent to the reactor effluent without contacting the spent catalyst. The effluent gas from the stripping zone and the cooling zone may be directed to the reactor effluent, or to the inlet of any upstream reactor.

Therefore, increases can be achieved through innovative flow schemes and equipment designs that allow for improved process control of the reactions. While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A process for regenerating a spent catalyst from a reactor comprising:
   passing the spent catalyst, having sulfur on the catalyst, to a sulfur stripping vessel;
   passing a hydrogen gas stream to the stripping vessel at an elevated temperature, thereby generating a stripped spent catalyst stream;
   passing the stripped spent catalyst stream to a regenerator, thereby generating a regenerated catalyst stream; and
   returning the regenerated catalyst to the reactor section via a reduction zone, wherein the reduction zone removes halogen compounds from the regenerated catalyst, thereby generating a reduction zone effluent gas.

2. The process of claim 1 further comprising passing the stripped spent catalyst stream to a catalyst cooler prior to passing the catalyst to the regenerator.

3. The process of claim 1 wherein at least 50% of the sulfur on the spent catalyst is removed in the sulfur stripping vessel.

4. The process of claim 2 wherein a cooling gas is passed at a temperature between 100° C. and 200° C.

5. The process of claim 3 wherein a cooling gas is passed at a temperature between 100° C. and 150° C.

6. The process of claim 1 wherein the stripping vessel temperature is at least 150° C.

7. The process of claim 6 wherein the stripping vessel temperature is at least 250° C.

8. The process of claim 1 wherein the halogen compound removed is chloride.

9. The process of claim 1 wherein the reduction zone effluent gas is directed to a cooling zone where the halogen compounds are adsorbed on the stripped catalyst in the cooling zone.

10. The process of claim 1 wherein the reactor is a dehydrogenation reactor, and the spent catalyst is a dehydrogenation catalyst.

11. A process for managing sulfur in a catalytic process comprising:
    passing a spent dehydrogenation catalyst stream to a stripping and cooling vessel;
    passing a sulfur free hydrogen rich gas having an elevated temperature to the stripping and cooling vessel, stripping the spent dehydrogenation catalyst of sulfur, thereby generating a stripped spent dehydrogenation catalyst that passes to a cooling section of the stripping and cooling vessel;
    passing a cooling gas to the stripping and cooling vessel to cool the stripped spent dehydrogenation catalyst, thereby generating a cooled catalyst stream;
    passing the cooled catalyst to a regenerator, to generate a regenerated catalyst;
    passing the regenerated catalyst to a reduction zone;
    passing the stripped spent dehydrogenation catalyst to a cooling zone, to generate a cooled spent catalyst and a cooling zone effluent gas, wherein the cooling zone removes halogen compounds from the cooling gas stream; and
    passing the cooled spent catalyst to the regenerator.

12. The process of claim 11 wherein at least 50% of the sulfur on the spent dehydrogenation catalyst is removed in the stripping and cooling vessel.

13. The process of claim 11 wherein the elevated temperature of the sulfur free hydrogen gas is at least 300° C.

14. The process of claim 12 wherein the cooling gas is passed at a temperature between 100° C. and 200° C.

15. The process of claim 14 wherein the cooling gas is passed at a temperature between 100° C. and 150° C.

16. The process of claim 11 wherein the reduction zone generates an effluent gas and the effluent gas is directed to the cooling section of the stripping and cooling vessel where the halogen compounds are absorbed on the stripped spent dehydrogenation catalyst in the cooling zone.

* * * * *